United States Patent
Deslandes et al.

(10) Patent No.: US 6,599,896 B1
(45) Date of Patent: Jul. 29, 2003

(54) USE OF TIANEPTINE IN THE PRODUCTION OF MEDICAMENTS TO TREAT NEURODEGENERATIVE PATHOLOGIES

(75) Inventors: Antoine Deslandes, Paris (FR); Michael Spedding, Le Vesinet (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/914,608

(22) PCT Filed: Apr. 6, 2000

(86) PCT No.: PCT/FR00/00865

§ 371 (c)(1),
(2), (4) Date: Aug. 30, 2001

(87) PCT Pub. No.: WO00/59511

PCT Pub. Date: Oct. 12, 2000

(30) Foreign Application Priority Data

Apr. 7, 1999 (FR) .......................................... 99 04313

(51) Int. Cl.$^7$ .............................................. A61K 31/553
(52) U.S. Cl. .................................................. 514/211.13
(58) Field of Search ..................................... 514/211.13

(56) References Cited

U.S. PATENT DOCUMENTS 5,888,542 A * 3/1999 Huet De Barochez et al. .. 424/464

FOREIGN PATENT DOCUMENTS

| FR | A-2 635461 | 2/1990 |
| FR | A-2 716623 | 1/1995 |

OTHER PUBLICATIONS

International Search Report for PCT/FR00/00865 with English translation (Jul. 2001).
B.S. Mcewen: "Stress effects on Morphology and function of the hippocampus" Ann. N.Y. Acad. Sci., vol. 821, 1997, pp. 271–284.

* cited by examiner

Primary Examiner—Raymond Henley, III
(74) Attorney, Agent, or Firm—The Firm of Hueschen and Sage

(57) ABSTRACT

The invention relates to the use of tianeptine or enantiomers thereof in obtaining medicaments for use in the treatment of neurodegenerative pathologies.

3 Claims, 5 Drawing Sheets

USE OF TIANEPTINE IN THE PRODUCTION OF MEDICAMENTS TO TREAT NEURODEGENERATIVE PATHOLOGIES

This is a 371 of PCT/FR00/00865 filed Apr. 6, 2000.

The present invention relates to the use of tianeptine, of isomers thereof and of salts thereof, in obtaining medicaments intended for the treatment of neurodegenerative pathologies.

Tianeptine, the compound of formula (I):

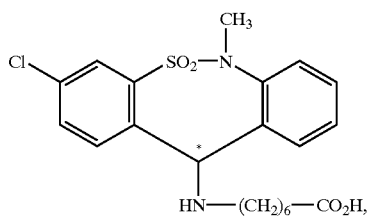

has been described in French Patent Specification FR 2 104 728 as a new medicament for use in the treatment of psychoneurotic disorders, pain and cough.

Furthermore, French Patent Specification FR 2 635 461 describes the use of tianeptine and compounds thereof in the treatment of stress.

Recent studies have shown that tianeptine has significant effects on memory. These are described by:

S. E. FILE et al. in: *Drug Development Research*, 1991, 23, 47–56;
R. Jaffard et al. in: *Journal de Psychiatrie Biologique et Thérapeutique*, 1989, March special edition, 37–39;
R. Jaffard et al. in: *Abstracts of the XVI$^{th}$ CINP Congress, Munich (Germany), 15–19, August 1988*; *Psychopharmacology*, 1988, 96 (suppl), 31.02.32, p. 275;
R. Jaffard et al. in: *Behavioural Pharmacology*, 1991, 2, 37–46;
C. Lebrun et al. in: *European Psychiatry*, 1993, 8 (suppl. 2), 81s–88s;
R. Jaffard et al. in: *Presse Médicale*, 1991, 20, 37, 1812–1816.

Finally, French Patent Specification FR 2 716 623 describes the use of the (+) isomer of tianeptine in obtaining medicaments intended for mnemo-cognitive disorders.

The Applicant has now discovered, surprisingly, that tianeptine is a modulator of glutamate receptors of the AMPA/kainate type and may therefore be used in the treatment of neurodegenerative pathologies.

L-glutamic acid and L-aspartic acid are capable of activating the neurons of the central nervous system, and numerous studies have demonstrated that these excitatory amino acids (EAAs) meet the defining criteria of a neurotransmitter; for this reason, modulation of the neuronal events associated with those EAAs appears to be a promising target for the treatment of neurological diseases.

Indeed, it has been proven that the excessive release of EAAs and hyperstimulation of their receptors could be one of the causes of the neuronal degeneration that is observed in epilepsy, senile dementia or cerebral vascular accidents. At the present time, the number of neurodegenerative diseases in which EAAs are strongly implicated is continually growing (Huntington's chorea, schizophrenia, amyotrophic lateral sclerosis) (Mc GEER E. G. et al., Nature, 263, 517–519, 1976; SIMON R. et al., Science, 226, 850–852, 1984).

Moreover, even though hyperactivation of EAA neurotransmission certainly produces neurotoxic effects, normal activation thereof facilitates mnemic and cognitive performance (LYNCH G. & BAUDRY M., Science, 224, 1057–1063, 1984; ROTHMAN S. M. & OLNEY J. W., Trends in Neuro Sci., 10, 299–302, 1987). From the pharmacological and therapeutic point of view, it is therefore appropriate to combat pathological stimulation only, whilst maintaining the level of physiological activation.

EAA receptors having a post- and pre-synaptic location have been classified into 4 groups as a function of the affinity for and electrophysiological and/or neurochemical effects of specific ligands:

the NMDA (N-methyl-D-aspartate) receptor, which is associated with an ion channel that is permeable to mono- and di-valent cations (including calcium) but blocked by magnesium. Accumulation of calcium and zinc in the cell might be one of the causes of neuron death. Opening of the NMDA channel is regulated by several sites associated with the receptor and, in particular, is facilitated by glycine, the effect of which is strychnine-insensitive. That glycine site represents an important target for modulating activation of the NMDA receptor.

the AMPA (α-amino-3-hydroxy-5-methyl-4-isoxazolepropionic acid) receptor, which is associated with an ion channel that is permeable to monovalent cations, including sodium. Activation of this channel might bring about membrane depolarisation.

the kainate receptor, the ionic characteristics of which are similar to those of the AMPA receptor but differ therefrom in the levels of conductance and desensitisation. Numerous studies tend to prove, however, that the AMPA receptor and the kainate receptor have close structural and functional analogies and constitute a single receptor family (KEINANEN K. et al., Science, 249, 556–560, 1990).

the ACPD (trans-1-aminocyclopentane-1,3-dicarboxylic acid) receptor, which is called the metabotropic receptor because it is not coupled to an ion channel.

Activation of the ionotropic receptors by EAAs opens the ion channels and especially allows the entry of sodium, which depolarises the cell. That first phase, which involves the AMPA receptor, then leads to disinhibition and, after that, hyperactivation of the NMDA receptor and massive accumulation of calcium (BLAKE J. F. et al., Neurosci. Letters, 89, 182–186, 1988; BASHIR Z. I. et al., Nature, 349, 156–158, 1991).

It has more especially been shown that tianeptine, in a novel manner, modulates the glutamatergic receptors of the AMPA/kainate type and could therefore be used in the treatment of neurodegenerative pathologies.

More specifically, the present invention relates to the use of tianeptine, enantiomers thereof and pharmaceutically acceptable salts thereof in obtaining pharmaceutical compositions intended for the treatment of neurodegenerative pathologies, such as cerebral ischaemia, cerebral traumatism, cerebral ageing, Alzheimer's disease, multiple sclerosis, amyotrophic lateral sclerosis, demyelinating pathologies, encephalopathies, chronic fatigue syndrome, myalgic encephalomyelitis, post-viral fatigue syndrome, the state of fatigue and depression following a bacterial or viral infection, and the dementia syndrome of AIDS.

Tianeptine and enantiomers thereof, optionally in the form of pharmaceutically acceptable salts, shall be presented in pharmaceutical forms that are suitable for administration by the oral, parenteral, per- or trans-cutaneous, nasal, rectal, perlingual, ocular or respiratory route, especially injectable preparations, aerosols, eye or nose drops, sublingual tablets, glossettes, soft gelatin capsules, hard gelatin capsules, lozenges, suppositories, creams, ointments, dermal gels etc., those forms allowing the immediate release or delayed and controlled release of the active ingredient.

The dosage varies according to the age and weight of the patient, the administration route, the nature of the therapeutic indication and associated treatments, and ranges from 12.5 mg to 300 mg per dose or per administration.

As bases that may convert tianeptine or enantiomers thereof into salts, there may be used, without implying any limitation, sodium hydroxide, potassium hydroxide, calcium hydroxide or aluminium hydroxide, alkali metal or alkaline earth metal carbonates, or organic bases such as triethylamine, benzylamine, diethanolamine, tert-butylamine, dicyclohexylamine, arginine etc.

As acids that may convert tianeptine or isomers thereof into salts, there may be used without implying any limitation, hydrochloric acid, sulphuric acid, phosphoric acid, tartaric acid, malic acid, maleic acid, fumaric acid, oxalic acid, methanesulphonic acid, ethanesulphonic acid, camphoric acid, citric acid etc.

The preferred salt of tianeptine is the sodium salt.

A—EFFECTS OF TIANEPTINE ON AMPA/KAINATE RECEPTORS

This experiment shows the effect of tianeptine at concentrations of 4, 10 and 25 $\mu$M on the current induced by kainate (250 $\mu$M) in telencephalic cells, in primary culture.

Experimental Protocol

Telencephalic cells of 16.5 day-old Wistar rat fetuses were cultured for 12 days. Patch clamp experiments were then conducted at ambient temperature in the following medium: 5 mM KCl, 140 mM NaCl, 10 mM Hepes, 2 mM $MgCl_2$, 2 mM $CaCl_2$ and 10 mM D-glucose (pH=7.3), and the micropipettes were filled with 140 mM KCl, 4 mM NaCl, 10 mM Hepes, 5 mM EGTA and 0.5 mM $CaCl_2$ (pH=7.2). Tianeptine (in the form of the sodium salt) was tested at concentrations of 4, 10 and 25 $\mu$M.

Results

Figure 1:
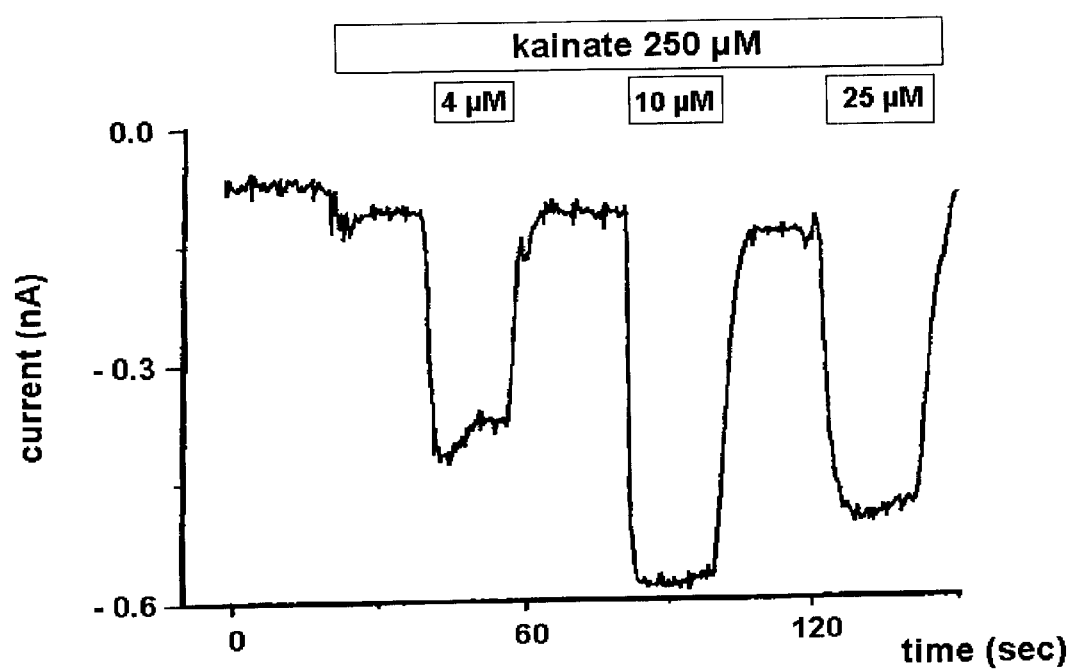
FIG. 1 shows the effect of tianeptine at concentrations of 4, 10 and 25 $\mu$M on the current induced by kainate (250 $\mu$M) in telencephalic cells, in primary culture, in patch clamp experiments.

In this experiment, kainate (an agonist of glutamatergic receptors of the AMPA/kainate type), in culture in telencephalic, cells, increases the current entering the cells. That effect is measured by the patch clamp technique. Tianeptine in its own (10 $\mu$M) has no effect under those conditions, it is therefore not a direct agonist. However, tianeptine (4, 10 and 25 $\mu$M) increases the current induced by kainate (250 $\mu$M), as shown in FIG. 1.

Consequently, tianeptine is a modulator of AMPA/kainate receptors.

B—EFFECT OF TIANEPTINE ON IN VITRO NEUROTOXICITY IN TWO MODELS THAT ARE PREDICTIVE OF NEUROTOXICITY

These experiments show the effects of tianeptine in models of neurotoxicity that are predictive of a neuroprotective effect for active ingredients in ischaemia, cerebral traumatism and neurodegeneration. The neurotoxicity of glutamate plays a major role in the pathogenesis of neuronal losses encountered in a number of pathological states (Choi, D. W. Trends Neurosci, 11, 465, 1988).

B—1 Effect of Tianeptine on Neurotoxicity Caused by Hypoxia

Experimental Protocol

Cortical cells are extracted from Sprague-Dawley rat foetuses and cultured in MEM (minimum essential medium) containing 5% horse serum and 5% calf foetus serum. The cultures are maintained at 37° C. in an atmosphere of 93% air and 7% $CO_2$. Just before hypoxia, the culture medium is replaced by 300 $\mu$l of saline solution buffered with HEPES (HCSS). The cells are incubated for 10 minutes under these conditions at ambient temperature. Tianeptine (in the form of the sodium salt) and MK-801 are added at different concentrations and the cells are incubated for 10 minutes. The culture media are then replaced by 300 $\mu$l of deoxygenated PIPES buffer at pH 7.4.

The cells are then incubated for 3 hours in a hypoxic atmosphere containing 95% $N_2$ and 5% $O_2$ at 37° C. The culture media are then replaced by 200 $\mu$l of MEM without serum and the cells are incubated again for 24 hours at 37° C. under standard conditions. After morphological examination of the cells, the culture supernatants are collected and the lactate dehydrogenase (LDH) activity therein is measured.

Results

Figure 2:
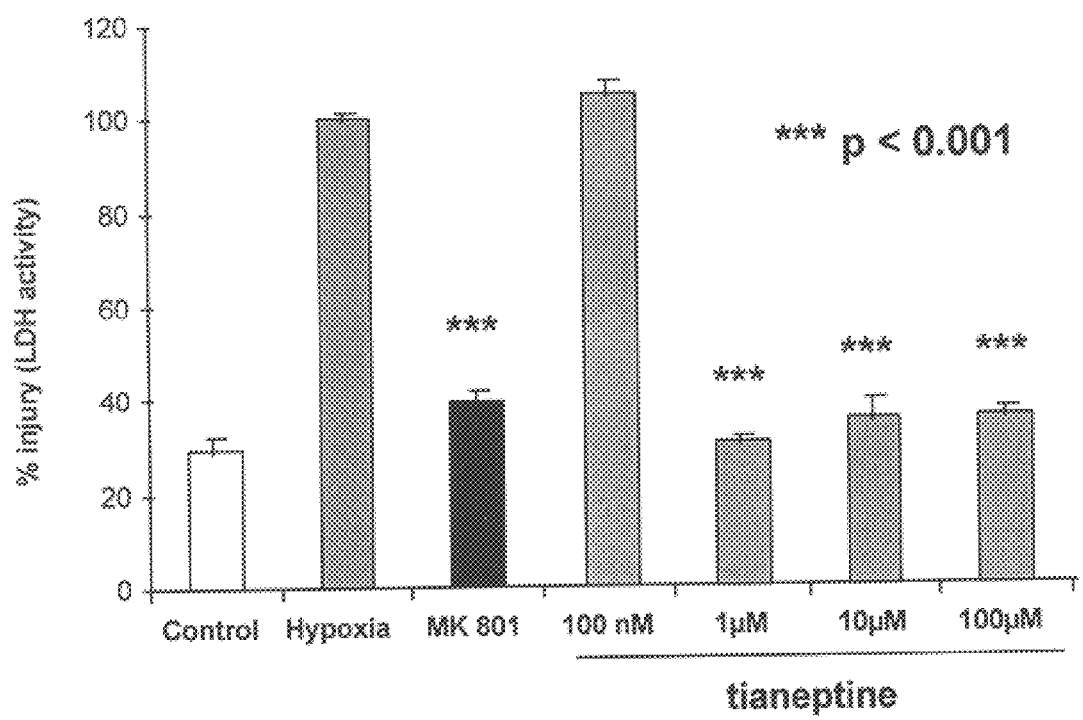
FIG. 2 presents the results of experiments demonstrating the effect of tianeptine on in vitro neurotoxicity caused by hypoxia.

Tianeptine, at concentrations of 1, 10 and 100 $\mu$M, significantly reduces the neurotoxicity caused by hypoxia, as shown in FIG. 2. The reduction in activity is 98.8, 91.7 and 91.4%, respectively. Under those conditions, MK-801 (20 $\mu$M), which is used as the neuroprotective agent of reference, brings about almost total (86.3%) protection against the effects of hypoxia.

Conclusion

Micromolar concentrations of tianeptine completely protect cortical neurons in culture from cell damage caused by hypoxia. Under these conditions it is as effective as the NMDA receptor antagonist of reference, MK-801.

B—2 Effect of Tianeptine on Neurotoxicity Caused by Glutamate

Experimental Protocol

Cortical cells are extracted from Sprague-Dawley rat foetuses and cultured in MEM (minimum essential medium) containing 5% horse serum and 5% calf foetus serum. The cultures are maintained at 37° C. in an atmosphere of 93% air and 7% $CO_2$.

Just before treatment with glutamate, the culture medium is replaced by 300 $\mu$l of saline solution buffered with HEPES. The cells are incubated for 15 minutes together with 1 mM glutamate. The culture media are then replaced by 200 $\mu$l of MEM without serum and the cells are incubated at 37° C. for 24 hours. After morphological examination of the cells, the culture supernatants are collected and the lactate dehydrogenase (LDH) activity therein is measured.

Results

Figure 3:
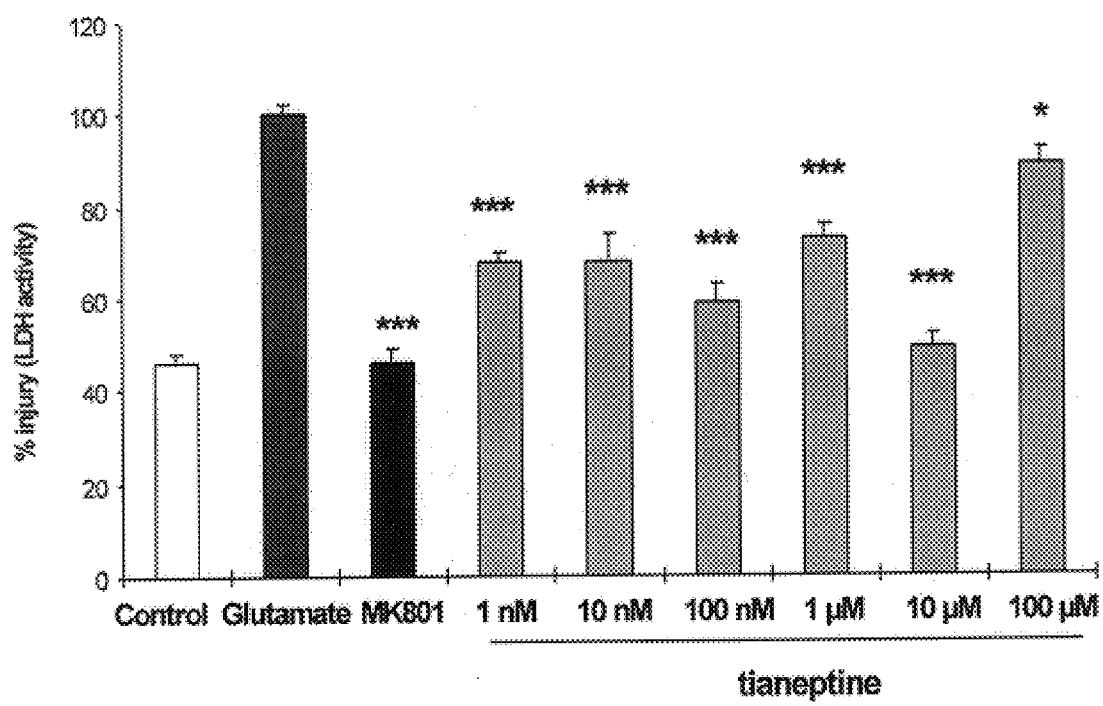
FIG. 3 presents the results of experiments demonstrating the effect of tianetpine on in vitro neurotoxicity caused by glutamate.

At concentrations of 1, 10, 100 nM and 1, 10, 100 μM, tianeptine significantly reduces the toxicity caused by glutamate, as shown in FIG. 3. The reduction in activity is between 59 and 94%. Under these conditions, MK-801 (20 μM), which is used as the protective agent of reference, brings about total protection against the effects of hypoxia.

Conclusion

Nanomolar concentrations of tianeptine are capable of protecting cortical neurons in culture against the degenerative effects caused by glutamate. These results indicate that tianeptine may act directly on the neurons to reduce their vulnerability to the damage caused by degenerative pathologies.

C—EFFECT OF TIANEPTINE ON LEVELS OF ADENOSINE TRIPHOSPHATE (ATP) ASSOCIATED WITH HYPOXIA IN ASTROCYTES MAINTAINED IN CULTURE

Experimental Protocol

Cultures of astrocytes are obtained using new-born rats according to the technique described by Booher J. and Sensenbrenner M. (Neurobiology 2, 97–105, 1992). They are used three weeks after being placed in culture. After adding culture medium (DMEM) that has been degassed in respect of $O_2$ and contains various concentrations of tianeptine, hypoxia is brought about in an anaerobic chamber for a period of 24 hours. The concentration of ATP is determined by luminescence and expressed in picomoles of ATP per mg of cellular proteins. The experiments are conducted in triplicate.

Results

Figure 4:
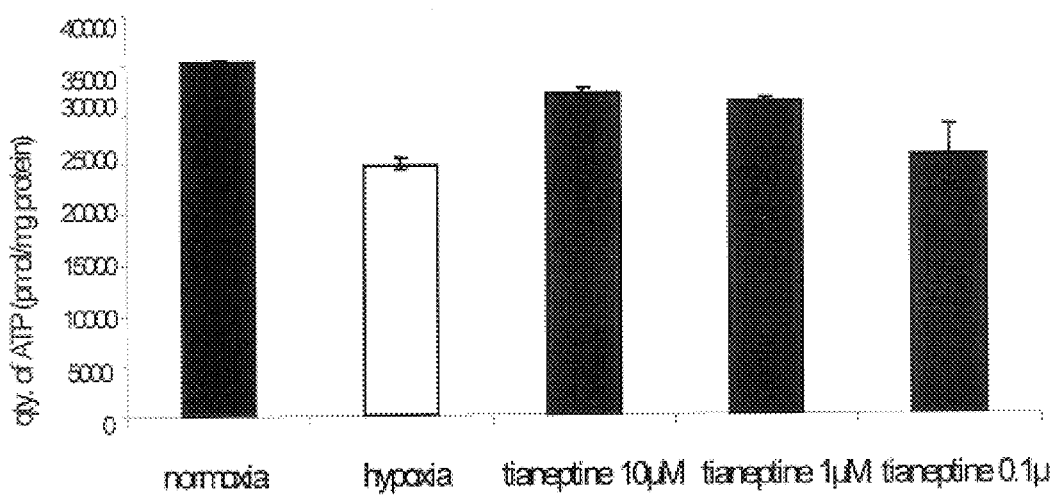
FIG. 4 presents the effect of tianeptine on levels of adenosine triphosphate (ATP) associated with hypoxia in astrocytes maintained in culture.

Tianeptine (0.1–1–10 μM) protects astrocytes in culture in a dose-dependent manner. The percentage protection is maximal at the 10 μM dose and reaches 68%. See FIG. 4.

Conclusion

Micromolar concentrations of tianeptine are capable of protecting astrocytes in culture against the degenerative effects caused by hypoxia.

D—NEUROPROTECTIVE EFFECT OF TIANEPTINE WITH RESPECT TO THE DEATH OF MOTONEURONS DEPRIVED OF GROWTH FACTORS

Experimental Protocol

Pregnant Sprague-Dawley rats are sacrificed on the 14th day of embryo life. The motoneurons of the embryos are purified according to the method published by C. E. Henderson ("Purified embryonic motoneurons" in "Nerve cell culture:a practical approach", J. Cohen and G. Wilkin, Eds, 1995, p. 69–81) and V. Aree et al. (J. Neurosci. Res., 1999, 55, p. 119–126).

The motoneurons are seeded a density of approximately 1000 cells per 16-mm well and are cultured in Neurobasal, supplemented by B27 and horse serum. After attachment of the motoneurons, the cells are incubated on their own, together with Brain-Derived Neurotrophic Factor (BDNF), 1 ng/ml or with tianeptine for 2½ days at 37.2° C. The surviving motoneurons are counted directly.

Results

Figure 5:
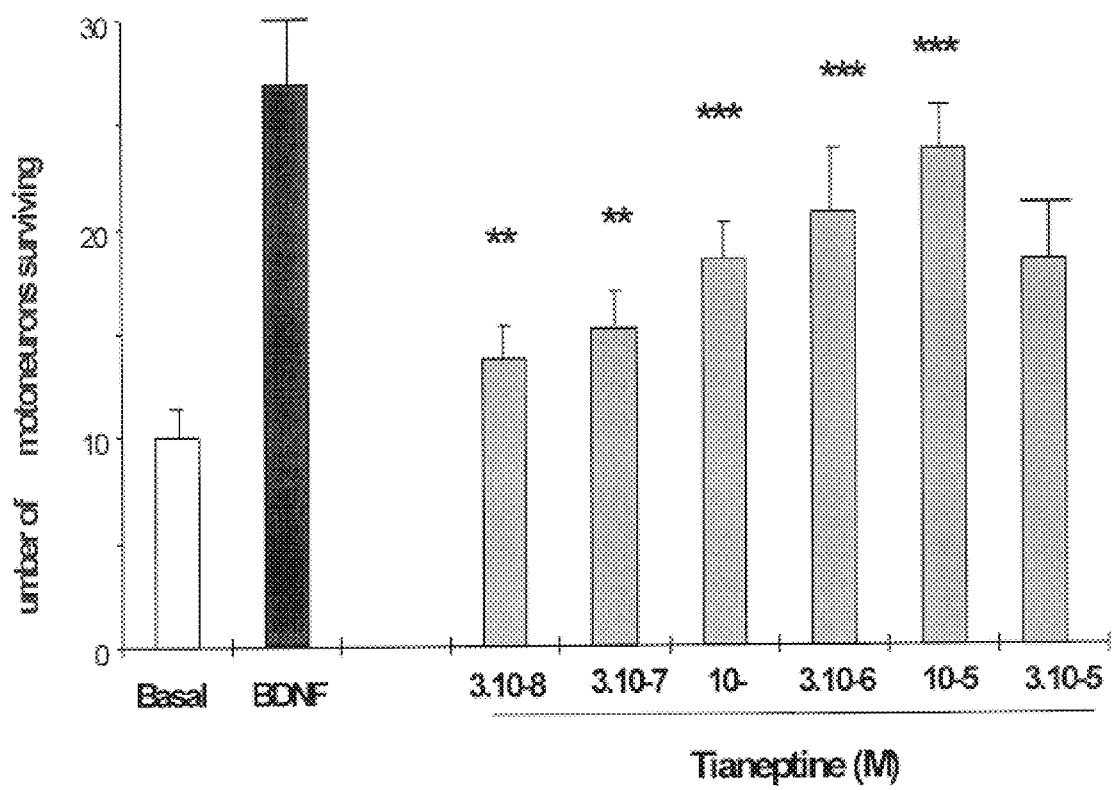
FIG. 5 presents the neuroprotective effect of tianeptine with respect to the death of motoneurons deprived of growth factors.

Growth factors are essential to the motoneurons because in the absence of BDNF the cells die. After 2.5 days of culture, motoneurons are counted in 2 areas of each of the 4 wells. Absolute value per area are presented (mean+/−s.e.m., n=8). BDNF protect the motoneurons from cell death. In a concentration-dependent manner, tianeptine prevents the motoneurons from dying (as shown in FIG. 5).

Conclusion

Using a similar model, Duong et al. (Br. J. Pharmacol., 128, 1385–1392) have shown that a product specifically known for its neuroprotective effects, SR57746A, was active. The authors concluded that "SR57746A was the only synthetic compound known to be active on the survival of motoneurons in vitro and thus was a good candidate compound for amyotrophic lateral sclerosis."

In this experiment we have shown that tianeptine has completely unexpected neuroprotective effects, indicating that tianeptine is likewise a potentially useful compound in the treatment of amyotrophic lateral sclerosis.

E—EFFECT OF TIANEPTINE IN VIVO ON THE EXPRESSION OF GENES IMPLICATED IN OXIDATIVE STRESS

The recent molecular biology technique of differential analysis by reverse transcription and then chain polymerisation reaction amplification (RT-PCR) has enabled the effects to be studied in vivo of treatment, on a chronic basis, with tianeptine with respect to genetic modulation at the central level, in the amygdala, in the rat.

Equipment and Methods

Two groups of rats (n=6) are treated with tianeptine sodium salt (15 mg/kg; i.p.) or physiological serum for 21 days. After sacrifice of the animals and removal of the brains, the total RNA of the amygdala region is extracted and then subjected to an RT-PCR test. In brief, reverse transcription is performed on the extracted RNA, the transcription products are then amplified by chain polymerisation (PCR) and then subjected to high-resolution polyacrylamide gel electrophoresis. The bands of interest are removed from the gel, re-amplified, sequenced and analysed.

Results

The results show that the prime target of tianeptine is the mitochondrial genome, which is composed of a circular DNA molecule of 16 kilobases coding for the 13 sub-units of the enzymatic complexes of the respiratory chain and for an entire series of ribosomal RNA and transfer RNA. Indeed, administration, on a chronic basis, of tianeptine causes the overexpression of the mitochondrial genes of NADH ubiquinone reductase (sub-units 2 and 5) and also of genes coding for 16S rRNA, leu-tRNA and val-tRNA.

NADH ubiquinone reductase is the first of the three enzymatic energy transfer complexes in the mitochondrial respiratory chain and represents the point of entry for the majority of electrons passing through that chain. Moreover, mutations of mitochondrial DNA are associated with a certain number of neurodegenerative diseases known under the overall name of mitochondrial encephalomyopathies (K. Chandrasekaran et al., Mol. Brain Res., 1994, 24:336–340; S. J. Kish et al., J. Neurochem., 1992, 59:776–779; E. M. Mutisaya et al., J. Neurochem., 1994, 63:2179–2184).

It has moreover been shown, using cultures of fibroblasts, that stress causes down-regulation of the levels of transcripts coding for the genes of sub-unit 4 of NADH, cytochrome b and sub-unit 165S of rRNA (D. R. Crawford et al., Free Radic. Biol. Med., 1997,22 (3):551–559).

Conclusion

The overexpression of the mitochondrial genes of the amygdala caused by administration, on a chronic basis, of tianeptine indicates that this compound increases the level of cell respiration and central oxidative metabolism. Such a central effect implies in vivo neuroprotective activity for tianeptine.

We claim:

1. A method for treating a living body afflicted with a neurodegenerative pathology selected from cerebral ischaemia, cerebral traumatism, cerebral aging, Alzheimer's disease, multiple sclerosis, amyotrophic lateral sclerosis, demyelating pathologies, encephalopathies, chronic fatigue syndrome, myalgic encephalomyelitis post-viral fatigue syndrome, the state of fatigue following a bacterial or viral infection, and the dementia syndrome of AIDS, consisting of the step of administering, as modulators of these receptors, to the living body an effective amount of a compound selected from tianeptine, its enantiomers, and its addition salts prepared with a pharmaceutically-acceptable acid or base.

2. The method of claim 1 in which the neurodegenerative pathology is amyotrophic lateral sclerosis.

3. The method of claim 1 in which tianeptine is in the form of a sodium salt.

* * * * *